United States Patent [19]

Beltzer et al.

[11] Patent Number: 5,019,283

[45] Date of Patent: May 28, 1991

[54] ENHANCING ANTIWEAR AND FRICTION REDUCING CAPABILITY OF CERTAIN XANTHATE CONTAINING MOLYBDENUM SULFIDE COMPOUNDS

[75] Inventors: Morton Beltzer; Jacob J. Habeeb, both of Westfield; James N. Francis, Maplewood, all of N.J.; Karla S. Colle, Houston, Tex.

[73] Assignee: Exxon Research and Engineering Company, Florham Park, N.J.

[21] Appl. No.: 404,141

[22] Filed: Sep. 7, 1989

[51] Int. Cl.$^5$ ............... C10M 135/14; C10M 141/06
[52] U.S. Cl. .................... 252/33.6; 252/42.7; 252/46.4; 252/49.7
[58] Field of Search ............ 252/25, 49.7, 46.3, 252/46.4, 33.6, 42.7

[56] References Cited

U.S. PATENT DOCUMENTS

| | | | |
|---|---|---|---|
| 2,951,040 | 8/1960 | Hugel | 252/33.6 |
| 3,419,589 | 12/1968 | Larson | 252/33.6 |
| 3,840,463 | 10/1974 | Froesehmann | 252/42.7 |

*Primary Examiner*—Jacqueline V. Howard
*Attorney, Agent, or Firm*—Joseph J. Dvorak

[57] ABSTRACT

It now has been discovered that lubricating compositions containing an additive formed by reacting Mo(CO)$_6$ with dixanthogen can be enhanced by the inclusion in the composition ligands selected from polydentate ligands and mixtures thereof. Thus, the present invention comprises a major amount of an aoil of lubricating viscosity and a minor but effective amount of an additive formed by reacting Mo(CO)$_6$ with dixanthogen of the formula (ROCS$_2$)$_2$ wherein R is an organo group having a sufficient number of carbon atoms to render the additive soluble in the oil; and a polydentate ligand or mixtures thereof, the mole ratio of additive to ligand being in the range of from about 1:1 to about 1:4.

9 Claims, No Drawings

ENHANCING ANTIWEAR AND FRICTION REDUCING CAPABILITY OF CERTAIN XANTHATE CONTAINING MOLYBDENUM SULFIDE COMPOUNDS

FIELD OF THE INVENTION

The present invention is concerned with improved lubricating compositions. More particularly, the present invention relates to lubricating compositions having xanthate containing molybdenum sulfide compounds as antiwear and antifriction additives. Indeed, this invention is concerned with enhancing the antiwear and friction reducing capability of such molybdenum compounds by including in the composition polydentate ligands.

BACKGROUND OF THE INVENTION

Molybdenum disulfide is a well-known lubricant additive. Because it is insoluble in lubricating oils, however, oil soluble sulfur containing molybdenum compounds have been proposed and investigated as lubricant additives. For example, in U.S. Pat. No. 2,951,040, an oil soluble molybdenum xanthate is disclosed as being useful in lubricating compositions. Apparently, the molybdic xanthate decomposes under conditions of use to form an oil insoluble solid molybdenum sulfide on the metal surfaces being lubricated.

U.S. Pat. No. 3,419,589 discloses the use of certain "sulfurized" molybdenum (IV) dialkyldithiocarbamates as lubricant additives. These additives are described as being oil soluble or at least capable of being easily suspended in oils.

U.S. Pat. No. 3,840,463 discloses the use of certain metal dialkyldithiocarbamates or dithiophosphates in combination with metal-free additives containing sulfur and phosphorus.

U.S. Pat. No. 4,588,829 discloses the use of (disulfido) tris (N, N-substituted dithiocarbamato) Mo(V) complexes in lubricant compositions.

In copending application Ser. No. 404,142, filed Sept. 7, 1989, there is disclosed a multifunctional additive formed by reacting molybdenum hexacarbonyl with dixanthogens of the formula $(ROCS_2)_2$ wherein R is an organo group having a sufficient number of carbon atoms to render the additive soluble in a base lubricating oil.

SUMMARY OF THE INVENTION

It now has been discovered that lubricating compositions containing an additive formed by reacting $Mo(CO)_6$ with dixanthogen can be enhanced by the inclusion in the composition ligands selected from polydentate ligands and mixtures thereof. Thus, the present invention comprises a major amount of an oil of lubricating viscosity and a minor but effective amount of an additive formed by reacting $Mo(CO)_6$ with dixanthogen of the formula $(ROCS_2)_2$ wherein R is an organo group having a sufficient number of carbon atoms to render the additive soluble in the oil; and a polydentate ligand or mixtures thereof, the mole ratio of additive to ligand being in the range of from about 1:1 to about 1:4.

This and other aspects of the present invention will be readily appreciated after reference to the Detailed Description, which follows.

DETAILED DESCRIPTION OF THE INVENTION

The lubricant compositions of the present invention include a major amount of oil of lubricating viscosity. This oil may be selected from naturally occurring mineral oils or from synthetic oils. The oils may range in viscosity from light distillate mineral oils to heavy lubricating oils, such as gas engine oil, mineral lubricating oil, passenger car oils and heavy duty diesel oils. In general, the viscosity of the oil will range from about 5 to about 26 centistokes at 100° C. and especially in the range of 10 to 18 centistokes.

The lubricant composition of the present invention includes a minor but effective amount of an additive formed by reacting molybdenum hexacarbonyl, $Mo(CO)_6$, with dixanthogen, $(ROCS_2)_2$. The reaction is conducted at temperatures ranging from about ambient room temperature to about 140.C and preferably at temperatures of about 80° C. to about 120° C. For example, the $Mo(CO)_6$ and the dixanthogen may be refluxed in toluene for times ranging from about 2 to about 8 hours.

The reaction time and temperature will depend upon the dixanthogen selected and the solvent used for carrying out the reaction.

Useful solvents for carrying out the reaction include aromatic hydrocarbons, especially toluene.

Suffice it to say that the reaction is conducted for a time sufficient to form the additive.

Dixanthogens especially useful in the practice of the present invention can be represented by the formula $(ROCS_2)_2$ in which R can be the same or different organo groups selected from alkyl, aralkyl and alkoxyalkyl groups having a sufficient number of carbon atoms to render the additive that is formed soluble in a lubricating oil. Preferably, R will have from 2 to 20 carbon atoms. Indeed, it is particularly preferred that R is an alkyl group having from 2 to 20 carbon atoms, and especially from 4 to 12 carbon atoms.

In forming the additive of the present invention, the mole ratio of dixanthogen to molybdenum hexacarbonyl should be greater than about 1.5 to 1. For example, in preparing the additive, it is preferred to use mole ratios of $(ROCS_2)_2$ to $Mo(CO)_6$ in the range of from about 1.6:1 to about 2:1.

Depending primarily upon the time and temperature at which the $Mo(CO)_6$ and $(ROCS_2)_2$ are reacted, the molybdenum and sulfur containing additive that forms is a brown compound, a purple compound or a mixture of both. Shorter reaction times, e.g., four hours or less, favor the formation of the purple compound. Longer reaction times, e.g., four hours or more, favor formation of the brown compound. For example, when $(C_8H_{17}OCS_2)_2$ is reacted with $Mo(CO)_6$ in toluene for four hours at 100° C. to 110° C., most of the starting material is converted to the purple compound, with virtually none of the brown being present. Continued heating of the reaction mixture results in conversion of the purple compound to the brown compound; indeed, after about six or seven hours, the purple form is largely converted to the brown.

In general, it is preferred to contact the $Mo(CO)_6$ and dixanthogen for a time sufficient for reaction to occur, but generally less than about 7 hours. Beyond 7 hours, undesirable solids begin to form. In order to maximize the formation of additive and minimize formation of undesirably solid by-products, it is preferred to react the $Mo(CO)_6$ and dixanthogen at temperatures of about 100° C. to about 120° C. for times ranging from about five to six hours, thereby producing reaction mixtures which contain both the brown and purple additives of this invention. This is no disadvantage because both forms are effective lubrication additives, and mixtures of the two species (brown and purple) perform as well as either species by itself.

The additives formed with R groups between about $C_4H_9$ and about $C_{14}H_{29}$ can be readily separated from oily organic by-products of the reaction by extracting the oily by-products with moderately polar solvents as acetone, ethyl alcohol, or iso-propyl alcohol. The additives with these R groups are substantially insoluble in such solvents, while the oily by-products are soluble. Separation of the additives from the by-products, however, is not necessary because the by-products do not detract from the beneficial functional properties of the additives.

The physical properties of the purple and brown additives vary with the R group. For example, the additive is crystalline solid when R is $C_2H_5$ and the additive is an amorphous solid when R is larger than about $C_7H_{15}$.

The purple compound formed in reacting $Mo(CO_6)$ with $(ROCS_2)_2$ is a thiocubane of the formula $Mo_4S_4(ROCS_2)_6$.

The brown compound formed in reacting $Mo(CO_6)$ with $(ROCS_2)_2$ is also believed to have a structure very similar to the thiocubane structure of the purple compound based on its ease of formation from the purple compound and chemical analysis.

The above described molybdenum-containing compounds are effective as additives in lubricating compositions when they are used in amounts ranging from about 0.01 to about 2.0 of weight percent, based on the weight of lubricating oil, and preferably at concentrations ranging from about 0.1 to about 1.0 weight percent.

Importantly, the lubricating composition of the present invention includes a polydentate ligand or mixtures hereof. Those skilled in the art know that the term "ligand" is used to designate functional coordinating groups which have one or more pairs of electrons available for the formation of coordinate bonds. Monodentate ligands can form only one bond with a metal ion, while polydentate ligands can form more than one bond with a metal ion. Polydentate ligands have been found to enhance the antiwear and friction reducing properties of the product obtained from $Mo(CO)_6$ and dixanthogens outlined above. Useful polydentate ligands include heterocyclic compounds in which nitrogen is the hetero atom like triazole, and dithiodipyridine. Particularly useful ligands in the practice of the present invention are nitrogen containing polydentate ligands having disulfide bonds like dithiodipyridine and thiadiazoles. Indeed, dithiodithiodipy dipyridine is most preferred.

In the practice of the present invention, the mole ratio of molybdenum containing additive to ligand will be in the range of from about 1:1 to about 1:4 and preferably in the range of from about 1:1 to about 1:2.

If desired, other known lubricant additives can be used for blending in lubricant compositions of this invention. These include ashless dispersants, viscosity improvers and the like. These can be combined in proportions known in the art.

The compositions of the present invention possess both antiwear properties and antifriction properties.

The invention will be more fully understood by reference to the following examples illustrating various modifications of the invention which should not be construed as limiting the claims herein.

EXAMPLE 1

This example illustrates the preparation of a purple molybdenum and xanthate containing additive for use in lube compositions according to the present invention.

A mixture of 717 grams (1.75 moles) of octyl dixanthogen, $(C_8H_{17}OCS_2)_2$, 263 grams (1 mole) of molybdenum hexacarbonyl, $Mo(CO)_6$, and two liters of toluene was heated to 100° C. with stirring sufficient to agitate the heavy $Mo(CO)6$ crystals, which did not completely dissolve. The temperature was gradually raised to 110° C. (refluxing the toluene) over a period of five hours, during which time 6 moles (about 150 liters) of carbon monoxide were liberated. The solution turned purple, and all the $Mo(CO)_6$ dissolved. The toluene was removed under a stream of nitrogen while maintaining the temperature of the solution below 800° C. A purple oil solidifying at about room temperature was obtained which was extracted twice with 10 times the volume of isopropyl alcohol containing 10% acetone. The alcohol insoluble solid was separated by filtration, washed with ten times its weight of cold hexane and then dried.

| Elemental Analysis | % Mo | % S | % C | % H |
|---|---|---|---|---|
| Found | 22.49 | 29.42 | 37.26 | 6.09 |
| Calc'd for $Mo_4S_4(C_8H_{17}OCS_2)_6$ | 22.04 | 29.39 | 37.20 | 5.86 |

X-ray structural analysis showed the product to be a thiocubane, $Mo_4S_4(C_8H_{17}OCS_2)_2$.

A chromatogram of the product was obtained as follows. A small spot of the sample was placed on a 2×6 cm piece of a commercially available silica gel chromatography medium. It was developed with a mixture of 30% toluene and 70% heptane. A dark purple spot at a retention factor (RF) of about 0.6 was observed, and a very faint brown spot remained near the origin.

EXAMPLE 2

This example illustrates the preparation of a brown molybdenum and xanthate containing additive suitable in lube compositions of the present invention.

The procedure of Example 1 was carried out, except that the reaction mixture was heated for a total of 7 hours. At the end of the heating time, the reaction mixture was allowed to cool to ambient temperature overnight. The mixture was filtered to remove any insoluble material formed, and the toluene removed and the brown residue was extracted as in Example 1. A thin layer chromatogram of the brown solid was obtained. The chromatogram, as in Example 1, showed little or no purple spot at a retention factor of 0.6, but a large dark brown spot near the origin.

Elemental analysis also was obtained with the results shown below.

| Elemental Analysis | % Mo | % S | % C | % H |
|---|---|---|---|---|
| Found | 26.23 | 31.91 | 34.38 | 5.61 |

EXAMPLE 3

This example illustrates the preparation of a mixed additive useful in compositions of the present invention.

The procedure of Example 1 was carried out, except that the reaction mixture was heated for a total of 6 hours. The toluene was removed as in Example 1 to yield a brownish-purple oil that partially solidifies upon standing at room temperature for some time. Chromatography as in Example 1 reveals the presence of both a purple spot at RF 0.6, and a brown spot near the origin. Exposure of the developed chromatogram to iodine vapors formed an orange-brown spot at RF 0.75 due to the organic by-products of the reaction mixture.

EXAMPLES 4 and 5

In these examples, lubricating compositions of the invention were evaluated for wear protection using the Four Ball Wear Test procedure (ASTM Test D2266). In all these tests, the base oil used was Solvent 150 Neutral. In all instances, the additive used was $Mo_4S_4(ROCS_2)_6$ wherein R is an octyl group. In one run, zinc dialkyldithiophosphate was present. The ligand used was 4,4′ dithiodipyridine, designated as DTDP in Table I. The compositions tested and the results are set forth in Table I.

TABLE I

| Run | Wt % $Mo_4S_4$ $(ROCS_2)_6$ | Wt % DTDP | Wt % ZDDP | Wear Volume in $mm^3 \times 10^4$ at 100° C., 1200 rpm 60 kg Load, 1 Hr. |
|---|---|---|---|---|
| 1. Example 4 | 0.1 | 0.02 | 0.0 | 10 |
| 2. Example 5 | 0.1 | 0.04 | 0.0 | 10 |
| 3. Comp. Ex. 6 | 0.0 | 0.0 | 0.0 | 464 |
| 4. Comp. Ex. 7 | 0.1 | 0.0 | 0.0 | 210 |
| 5. Comp. Ex. 8 | 0.1 | 0.0 | 0.04 | 188 |

COMPARATIVE EXAMPLES 6 to 8

The Four Ball Wear Test was repeated using Solvent 150 Neutral (Comp. Ex. 6), Solvent 150 Neutral and the multifunctional additive $Mo_4S_4(ROCS_2)_6$ (Comp. Ex. 7), and Solvent 150 Neutral with ZDDP (Comp. Ex. 8). The results are also shown in Table I.

What is claimed is:

1. A method of enhancing the antiwear and friction reducing properties of a lubricating oil composition comprising an oil of lubricating viscosity and a molybedenum and xanthate containing additive formed by reacting $Mo(CO)_6$ with a dixanthogen of the formula $(ROCS_2)_2$ wherein R is an organo group having a sufficient number of carbon atoms to render the additive soluble in the oil, the method comprising: adding to said oil composition a polydentate ligand or mixtures thereof.

2. The method of claim 1 wherein the mole ratio of additive to ligand is in the range of from about 1:1 to about 1:4.

3. The method of claim 2 wherein R is selected from alkyl, aralkyl and alkoxyalkyl groups having from about 2 to about 20 carbon atoms, the mole ratio of dixanthogen to $Mo(CO)_6$ is from about 1.5:1 to about 2:1.

4. The method of claim 3 wherein the polydentate ligand is a nitrogen containing heterocyclic compound in which nitrogen is the hetero atom.

5. The method of claim 4 wherein the ligand is a dithiodipyridine.

6. A method of enhancing the antiwear and friction reducing properties of a lubricating composition comprising an oil of lubricating viscosity and an additive having the formula $Mo_4S_4(S_2C-OR)_6$ wherein R is selected from organo groups having sufficient number of carbon atoms to render the additive soluble in oil, the method comprising: adding to the lubricating composition a ligand selected from polydentate ligands of nitrogen containing heterocyclic compounds, the mole ratio of additive to ligand being in the range of from about 1:1 to about 1:4.

7. The method of claim 6 wherein R is selected from alkyl, aralkyl and alkoxyalkyl groups having from about 2 to about 20 carbon atoms, the mole ration of dixanthogen to $Mo(CO)_6$ is from about 1.5:1 to about 2:1.

8. A method for improving a lubricating composition comprising an oil selected from natural and synthetic oils of lubricating viscosity and an additive composition formed by contacting $Mo(CO)_6$ and a dixanthogen of the formula $(ROCS_2)_2$ in the ratio of about 1.5:1 to 2:1 at temperatures in the range of from about ambient room temperature to about 140° C. for about 2 to about 10 hours, wherein R in the dixanthogen is selected from alkyl, aralkyl and alkoxyalkyl groups having from about 2 to 20 carbon atoms, the method comprising: adding to the composition a ligand selected from nitrogen containing heterocyclic polydentate ligands or mixtures thereof in which the nitrogen is the hetero atom, the ratio of ligand or mixture of ligands to additive being about 1:1 to about 1:4.

9. The method of claim 8 wherein the ligand is dithiodipyridine.

* * * * *